United States Patent [19]

Asai et al.

[11] Patent Number: 4,637,399
[45] Date of Patent: Jan. 20, 1987

[54] WATERPROOF ELECTRODE FOR RECORDING ELECTROCARDIOGRAM

[75] Inventors: Toshio Asai, Uchinadamachi; Yasuhiro Nakaya, Kanazawashi, both of Japan

[73] Assignee: Fukuda Denshi Co., Ltd., Tokyo, Japan

[21] Appl. No.: 742,822

[22] Filed: Jun. 10, 1985

[30] Foreign Application Priority Data

Jun. 11, 1984 [JP] Japan ............................. 59-120379

[51] Int. Cl.[4] .............................................. A61B 5/04
[52] U.S. Cl. .................................. 128/639; 128/640; 128/643
[58] Field of Search ..................... 128/639, 643, 903

[56] References Cited

U.S. PATENT DOCUMENTS

| 3,568,663 | 3/1971 | Phipps | 128/643 |
| 3,595,218 | 7/1971 | Kirkpatrick | 128/643 |
| 4,515,162 | 5/1985 | Yamamoto et al. | 128/643 |

FOREIGN PATENT DOCUMENTS 1466834  3/1969  Fed. Rep. of Germany ...... 128/903

Primary Examiner—Kyle L. Howell
Assistant Examiner—Randy Citrin
Attorney, Agent, or Firm—Pollock, VandeSande & Priddy

[57] ABSTRACT

Waterproof electrodes for recording an electrocardiogram, in which one end of a lead wire is inserted from the convex surface side to the concave surface side of a cup-shaped suction disc made of waterproof elastic material into a through hole formed at the center of the disc, an electrode plate connected to the end of the lead wire is put on the concave surface side of the suction disc to close the hole, the contacting portion between the outer peripheral edge portion of the plate and the concave surface of the suction disc and the gap between the periphery of the wire and the convex surface of the suction disc are respectively hermetically sealed by elastic sealing material, and an annular body surface adherent sheet capable of hermetically sticking on the surface of a human body along the concentric circle surrounding the electrode plate is bonded on the concave surface of the disc.

1 Claim, 4 Drawing Figures

WATERPROOF ELECTRODE FOR RECORDING ELECTROCARDIOGRAM

FIELD OF THE INVENTION

The present invention relates to a waterproof electrode for recording an electrocardiogram used to study the function of a heart during exercise in the water, such as swimming or rehabilitation.

BACKGROUND OF THE INVENTION

As a result of the recent developments in medical techniques and the general medical care of hearts, a number of serious and mild cardiac diseases have been discovered and aided by the cardiac therapy.

However, mild cardiac patients, particularly mild cardiac sick children discovered at school by cardiac examination conducted nationwide are prevented from joining swimming training as being too severe an exercise, in some cases.

In conventional infant circulatory organ science, the reason that the mild cardiac infant cannot swim safely is based on the result of consideration of the energy consumption and the measured result of inspection of the electrocardiogram of the infants recorded on the ground. So far, there has been no electrode for recording the electrocardiogram during swimming. Therefore, the swimming restrictions are not based on the result of the inspection of the electrocardiogram during actual swimming.

However, the circulatory action during swimming is different from that during the exercises on the ground, and abnormal variations are observed during swimming, since accurate circulatory action of a pupil during swimming cannot be determined at present, safety of the mild cardiac sick pupil cannot be therefore confirmed. It is difficult to give approval of swimming to the mild cardiac sick pupil who has to be allowed to swim, based on the conventional inspection.

Then, it becomes necessary to prove that the pupil can safely swim by recording the electrocardiogram during actual swimming.

In order to record the electrocardiogram of the human body during swimming, it is necessary to detect ultrafine current induced on the skin of the human body during swimming by electrodes attached on the skin, and to lead said current to an electrocardiograph on the ground to measure the variation in the potential generated in the human body.

Since the electrodes attached on the skin of the living body are easily separated from the skin in the water, the electrodes may be bonded with adhesive or bonding agent on the skin in some cases. However, it is troublesome to bond the electrodes on the skin and it gives a load for an examinee. Even if the electrodes were bonded with adhesive on the skin, they can be separated from the skin during severe swimming exercise. Further, since the waterproofness of the electrodes may not be adequate, there is a drawback or a disadvantage that a good electrocardiogram cannot be obtained.

SUMMARY OF THE INVENTION

It is therefore an object of this invention to provide a waterproof electrode for recording an electrocardiogram which has reduced or eliminated the foregoing drawbacks or disadvantage.

According to the present invention, there is provided a waterproof electrode for recording an electrocardiogram comprising a cup-shaped suction disc made of waterproof elastic material which has a through hole at the center thereof, an electrode plate for detecting an electrocardiac signal which is put on the concave surface side of said suction disc to close said through hole, a lead wire which has one end inserted from the convex surface side to the concave surface side of said suction disc through said through hole and connected to the electrode plate, elastic sealing members for hermetically sealing the contacting portion between the outer peripheral edge portion of said electrode plate and the concave surface of said suction disc and the gap between the periphery of said wire and convex surface of the disc respectively, and an annular body surface adherent sheet put on the concave surface of the suction disc for hermetically sticking to the surface of a human body along the concentric circle surrounding said electrode plate.

DETAILED DESCRIPTION OF THE INVENTION

The present invention will be described in detail in the embodiment shown in the accompanying drawings.

DETAILED DESCRIPTION OF THE INVENTION

Figure 1:
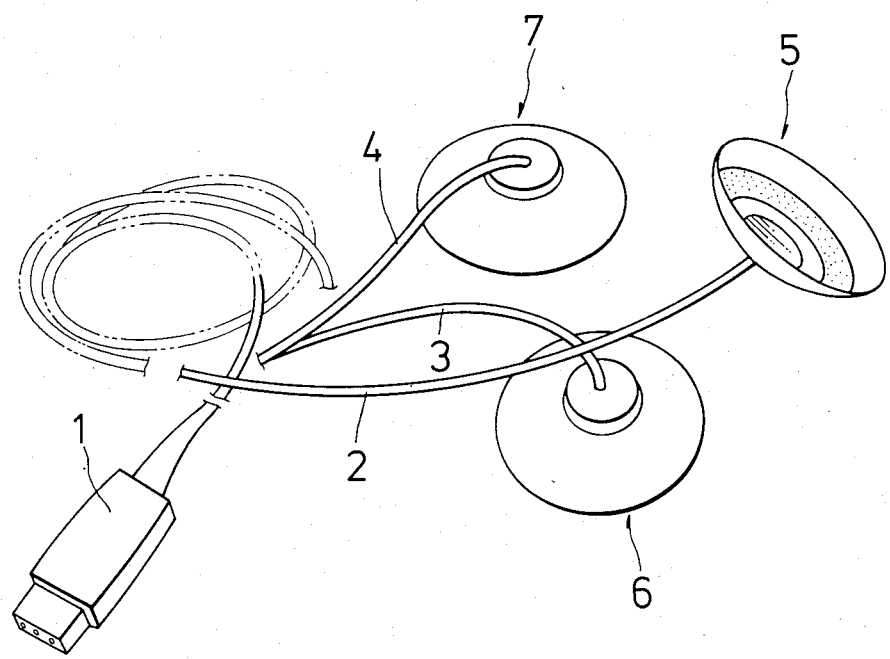
FIG. 1 is a perspective view showing a combination of electrodes and lead wires.
Figure 4:
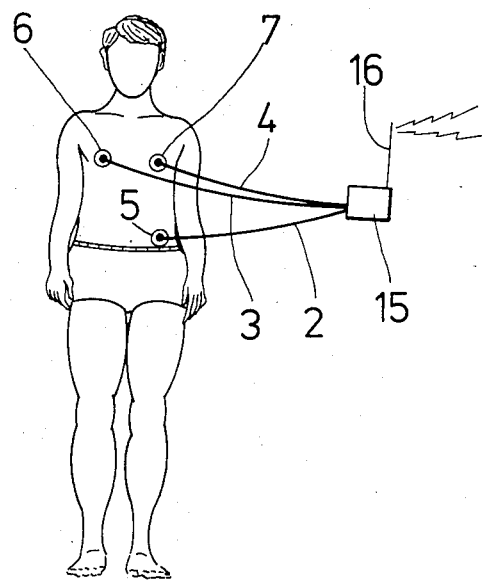
FIG. 4 is a view of the electrodes attached on a human body.

In FIG. 1, which shows a combination of electrodes and lead wires according to the present invention, reference numeral 1 designates a connector. Three lead wires 2, 3, 4 are connected to one end of the connector 1, and a transmitter 15 with an antenna 16 is connected to the other end as shown in FIG. 4.

Electrodes 5, 6, 7 are connected with the other ends of the three lead wires 2, 3, 4, respectively.

Figure 2:
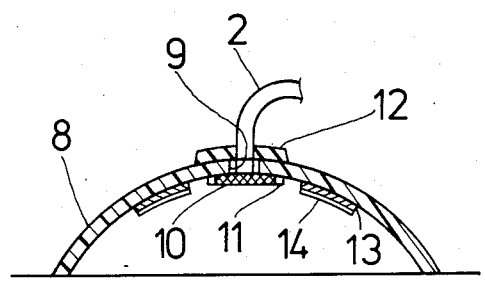
FIG. 2 is a longitudinal sectional view of the electrodes of FIG. 1.
Figure 3:
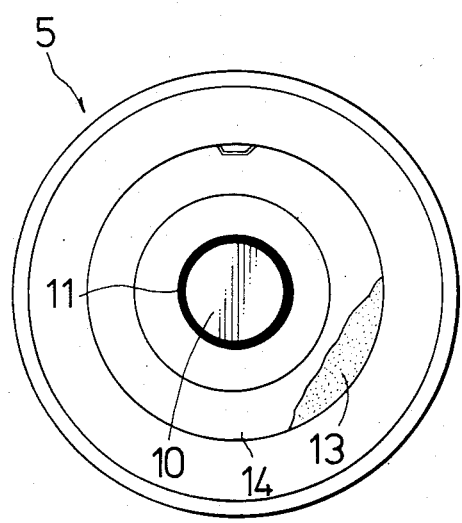
FIG. 3 is a plan view of the electrode of FIG. 2.

Since the construction of the electrodes 5, 6, 7 are identical, the construction of the electrode 5 only will be described with reference to FIGS. 2 and 3. The electrode 5 has a cup-shaped suction disc made of waterproof synthetic resin elastic material. A through hole 9 is formed at the center of the suction disc 8, and one end of the lead wire 2 is inserted from the convex side of the suction disc 8 into the hole 9 toward the concave side. An electrode plate 10 is connected to the one end of the lead wire 2 and placed on the concave side of the suction disc 8 to close the hole.

A contacting portion between the outer periphery portion of the plate 10 and the concave surface of the suction disc 8 is hermetically sealed with elastic sealing material 11 such as silicone rubber. A gap between the periphery of the lead wire 2 and the convex surface of the sucking disc 8 is hermetically sealed with an elastic sealing material 12 such as a silicone rubber, thereby preventing immersion in water from the outer surface of the suction disc 8. An annular body surface adherent sheet 14 is bonded with bonding agent 13 along the concentric circle surrounding the plate 10 on the concave surface of the suction disc 8, and the bonding agent is coated also on the surface of the adherent sheet 14.

Putting the electrodes 5, 6, 7 described above on suitable positions of the skin surface of a body as shown in FIG. 4, and pressing the suction disc 8, the adherent sheet 14 bonded on the concave surface of the suction disc 8 adheres on the skin surface of the body, and a suction force caused by returning action of the suction disc 8 to its original shape acts on the suction disk 8, the electrodes can be so firmly attached on the skin surface of the body that the electrodes are not separated from the body even in strenuous exercise such as swimming.

According to the present invention as described above, since the electrode comprises the cup-shaped suction disc and the body surface adherent sheet which is bonded on the concave surface of the cup-shaped suction disc, the electrodes can reliably be attached on the outer surface of the human body due to the bonding force of the adherent sheet and the suction force caused by returning action of the suction disc to its original shape, so that the electrodes are not separated from the body even during severe exercise in water, such as swimming.

Since the electrodes comprise the cup-shaped suction disc, the electrodes are attached on the outer surface of the body merely by pressing the suction disc against the outer surface of the body. Thus, excessive labor such as bonding the electrodes with adhesive on the body can be eliminated, and the electrodes can be easily bonded without the load for the examinee.

Further, the cup-shaped suction disc is made of waterproof elastic material, and the contacting portion between the outer peripheral edge portion of the electrode plate and the concave surface of the disc, and the gap between the peripheral surface of the lead wires and the convex surface of the disc are hermetically sealed by the elastic seals. Thus, the electrodes according to the present invention have advantages that its waterproofness is reliable and durable.

While the present invention has been described in detail with respect to a certain preferred embodiment of the invention, it will be understood by those skilled in the art that various changes and modifications may be made without departing from the spirit and scope of the invention, and it is intended therefore to cover all such changes and modifications in the appended claims.

What is claimed is:

1. A waterproof electrode for detecting an electrocardiac signal comprising:
   (a) a cup-shaped suction disc constructed from a waterproof, elastic material, said disc having a concave side, a convex side and a through-hole at the center thereof;
   (b) an electrode plate having an outer peripheral edge hermetically sealed to the concave surface of said suction disc and closing said through-hole;
   (c) a lead wire connecting to said electrode plate and extending through said through-hole and past the convex surface of said suction disc;
   (d) elastic sealing means for hermetically sealing together the outer peripheral edge of said electrode plate and the portions of the concave surface of said suction disc in contact with said peripheral edge of said electrode plate;
   (e) elastic sealing means hermetically sealing the lead wire at the convex surface of the suction disc; and,
   (f) an annular, body-surface adherent strip surrounding said electrode plate and bonded to said concave side of said disc.

* * * * *

UNITED STATES PATENT AND TRADEMARK OFFICE
CERTIFICATE OF CORRECTION

PATENT NO. : 4,637,399
DATED : January 20, 1987
INVENTOR(S) : Toshio Asai, et al.

It is certified that error appears in the above—identified patent and that said Letters Patent is hereby corrected as shown below:

Column 1, line 18, change "examination" to --examinations--;

Column 1, line 45, change "current" to --currents--;

Column 1, line 66, change "disadvantage" to --disadvantages--;

Column 2, line 59, change "sucking" to --suction--;

Column 4, line 20, change "connecting" to --connected--.

Signed and Sealed this

Fifteenth Day of September, 1987

Attest:

DONALD J. QUIGG

*Attesting Officer*      *Commissioner of Patents and Trademarks*